United States Patent
Lees et al.

(10) Patent No.: US 6,340,345 B1
(45) Date of Patent: Jan. 22, 2002

(54) SURGICAL RETRACTOR BLADE AND HANDLE FOR MOVEMENT WITH TWO DEGREES OF FREEDOM

(75) Inventors: John Lees, Richmond, VA (US); Jerry M. Brown, Sewaren, NJ (US); Gregory Diamont, New York, NY (US)

(73) Assignee: Automated Medical Products Corp., Sewaren, NJ (US)

( * ) Notice: Subject to any disclaimer, the term of this patent is extended or adjusted under 35 U.S.C. 154(b) by 0 days.

(21) Appl. No.: 09/513,139

(22) Filed: Feb. 25, 2000

Related U.S. Application Data
(60) Provisional application No. 60/124,932, filed on Mar. 18, 1999.

(51) Int. Cl.[7] .............................................. A61B 17/02
(52) U.S. Cl. ...................................... 600/226; 600/229
(58) Field of Search ................................ 600/213, 210, 600/235, 232, 233, 226, 228, 229

(56) References Cited

U.S. PATENT DOCUMENTS

| | | | |
|---|---|---|---|
| 3,129,706 A | * | 4/1964 | Reynolds, Jr. ............ 600/233.2 |
| 3,227,156 A | * | 1/1966 | Gauthier .................. 600/232.2 |
| 3,339,913 A | | 9/1967 | Anderson |
| 3,542,015 A | * | 11/1970 | Steinman .................... 600/229 |
| 4,143,652 A | | 3/1979 | Meier et al. |
| 4,461,284 A | | 7/1984 | Fackler |
| 4,491,435 A | | 1/1985 | Meier |
| 4,718,151 A | | 1/1988 | LeVahn et al. |
| 4,796,846 A | | 1/1989 | Meier et al. |
| 4,945,897 A | | 8/1990 | Greenstein et al. |
| 5,025,780 A | | 6/1991 | Farley |
| 5,162,039 A | | 11/1992 | Dahners |
| 5,224,680 A | | 7/1993 | Greenstein et al. |
| 5,365,921 A | | 11/1994 | Bookwalter et al. |
| 5,441,042 A | | 8/1995 | Putman |
| 5,529,571 A | | 6/1996 | Daniel |
| 5,538,215 A | | 7/1996 | Hosey |
| 5,662,300 A | | 9/1997 | Michelson |
| 5,755,412 A | | 5/1998 | Guibert et al. |
| 5,865,731 A | * | 2/1999 | Lenox et al. ............ 600/232.2 |
| 5,876,332 A | | 3/1999 | Looney |
| 5,902,233 A | * | 5/1999 | Farley et al. ............ 600/213.2 |
| 5,908,382 A | * | 6/1999 | Koros et al. ............ 600/232.2 |
| 5,931,777 A | | 8/1999 | Sava |
| 5,944,658 A | * | 8/1999 | Koros et al. ............ 600/232.2 |
| 5,976,080 A | * | 11/1999 | Farascionl ............... 600/213.2 |
| 5,984,865 A | * | 11/1999 | Farley et al. ............ 600/213.2 |

FOREIGN PATENT DOCUMENTS
WO    WO 97/40752    11/1997

OTHER PUBLICATIONS
A.C. Stieber, Hepatic Transplantation With the Aid of the Iron Intern Retractor, The American Journal of Surgery, vol. 160, pp. 300–301, Sep. 1990.

R.J. Greenstein, Mechanical Retraction in Obesity and Esophagogastric Surgery, vol. 1, pp. 431–433, 1991.

* cited by examiner

Primary Examiner—Paul J. Hirsch
(74) Attorney, Agent, or Firm—Blank Rome Comisky & McCauley LLP

(57) ABSTRACT

A surgical retractor blade is attached to a ratchet handle with a ball and socket joint to move with more than one degree of freedom. The surgical retractor blade can be removably attached to the handle through either a slot on the handle or a clamping mechanism attached to the handle by the ball and socket joint. In the case of the slot, the surgical retractor blade has a shaft with a first diameter narrower than the slot and a second diameter wider than the slot. The blade is turned one way for attachment and removal and another way to secure it to the handle for use.

3 Claims, 4 Drawing Sheets

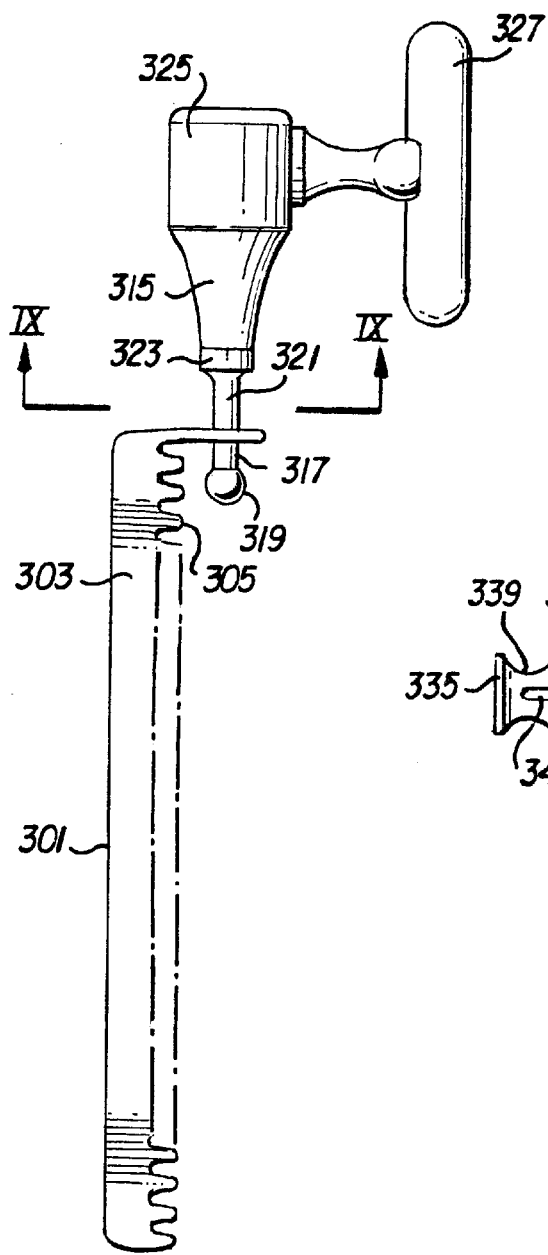
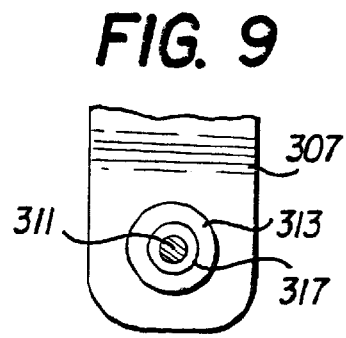
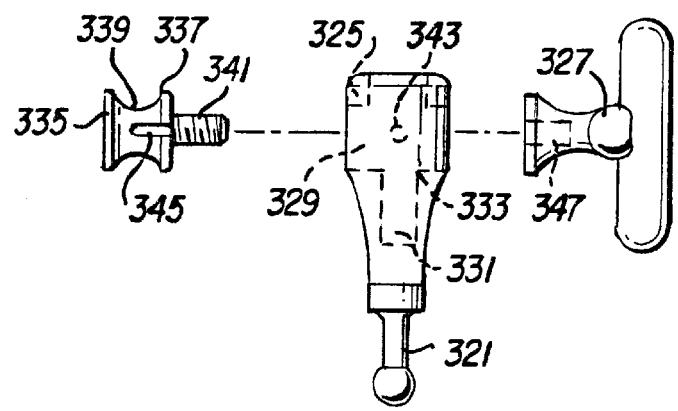
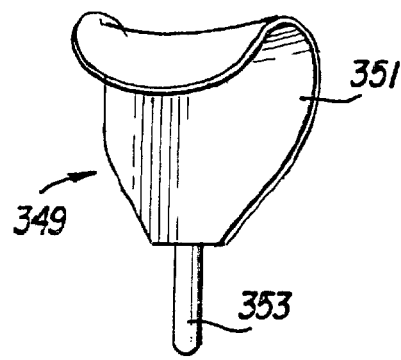

SURGICAL RETRACTOR BLADE AND HANDLE FOR MOVEMENT WITH TWO DEGREES OF FREEDOM

REFERENCE TO RELATED APPLICATION

This application claims the benefit of U.S. Provisional Application No. 60/124,932, filed Mar. 18, 1999, whose disclosure is hereby incorporated by reference into this disclosure.

FIELD OF THE INVENTION

The present invention is directed to a retractor blade for use in surgery, a ratcheted blade holder for holding the blade to allow movement with two degrees of freedom, and the combination of the two.

DESCRIPTION OF RELATED ART

It is known in the surgical arts to provide access to certain body parts during surgery by providing devices to hold certain other body parts out of the way. For example, during a liver transplant, it is often necessary to hold the rib cage up and the stomach out of the way; retaining devices having retaining blades at their ends can be attached to the above-mentioned horizontal bar to perform those functions. A well known example of that technology is a Stieber Grip sold by the assignee of the present application and shown in FIG. 1.

The Stieber Grip 101 is secured to the surgical table by a pair of clamping devices shown in dotted lines and is positioned over the patient P to hold the patient's stomach and rib cage out of the way to allow access to the liver (internal organs not being shown in detail in FIG. 1). The assembly 101 includes, inter alia, sliding platforms 103 with ratchet mechanisms 105 for holding ratchet handles 107 with blades 109 on their ends. The ratchet engagement between the ratchet mechanisms 105 and the ratchet handles 107 allows the blades 109 to be set at desired positions, e.g., to accommodate various types of operations or patients P of various sizes. That engagement also allows the handles 107 and blades 109 to be removed altogether to insert blades 109 of different sizes or different devices altogether. The rest of the assembly and the details of its use will be readily apparent to those skilled in the art.

FIG. 2 shows the handle 107 and blade 109 in detail. As can be seen, blades 109 of various sizes and shapes can be provided. However, the blades 109 are permanently attached to the handles 107 by pivot attachments 111. Also, the pivot attachments 111 allow rotation of the blades 109 only in a single plane, or in other words with a single degree of freedom.

The following references show such blades, and the disclosures of those references are hereby incorporated by reference in their entireties into the present disclosure: U.S. Pat. No. 4,143,652, issued to Meier et al on Mar. 13, 1979; U.S. Pat. No. 4,945,897, issued to Greenstein et al on Aug. 7, 1990; A. C. Stieber, "Hepatic Transplantation with the Aid of the Iron Intern Retractor," *The American Journal of Surgery*, Vol. 160, pp. 300–01, September, 1990; and R. J. Greenstein, "Mechanical Retraction in Obesity and Esophagogastric Surgery," *Obesity Surgery*, Vol. 1, pp. 431–433, 1991.

SUMMARY OF THE INVENTION

In light of the above, it will be readily apparent that a need exists in the art for a surgical retractor blade that can move relative to its handle in more than simply a single plane, or in other words in two degrees of freedom. To this end, a primary object of the invention is to provide a surgical retractor blade that is attached to its handle for two degrees of freedom.

A further object of the invention is to provide a surgical retractor blade that is removable from its handle.

To achieve these and other objects, the present invention is directed to a surgical retractor blade and ratchet handle that are attached with a joint that allows two degrees of freedom, such as a ball-and-socket joint. The blade is rendered removable in different ways in two preferred embodiments. In one preferred embodiment, the ball-and-socket joint is configured so that the blade is normally held in the joint but can be removed as needed. The removal operation involves a relative movement between the blade and the handle that will not occur while the blade in use, so that the blade will not come off during surgery. In another preferred embodiment, the ball-and-socket joint permanently attaches a holder to the handle, and the blade is removably attached to the handle.

BRIEF DESCRIPTION OF THE DRAWINGS

Two preferred embodiments of the present invention will be set forth in detail with reference to the drawings, in which:

FIG. 8 shows a ratchet handle and attachment portion according to a second preferred embodiment of the present invention;

FIG. 9 shows a cross-sectional view of a portion of the attachment portion of FIG. 8;

FIG. 10 shows an exploded view of the attachment portion of FIG. 8; and

FIG. 11 shows a blade for use with the handle and attachment portion of FIG. 8.

DETAILED DESCRIPTION OF THE PREFERRED EMBODIMENTS

Figure 1:
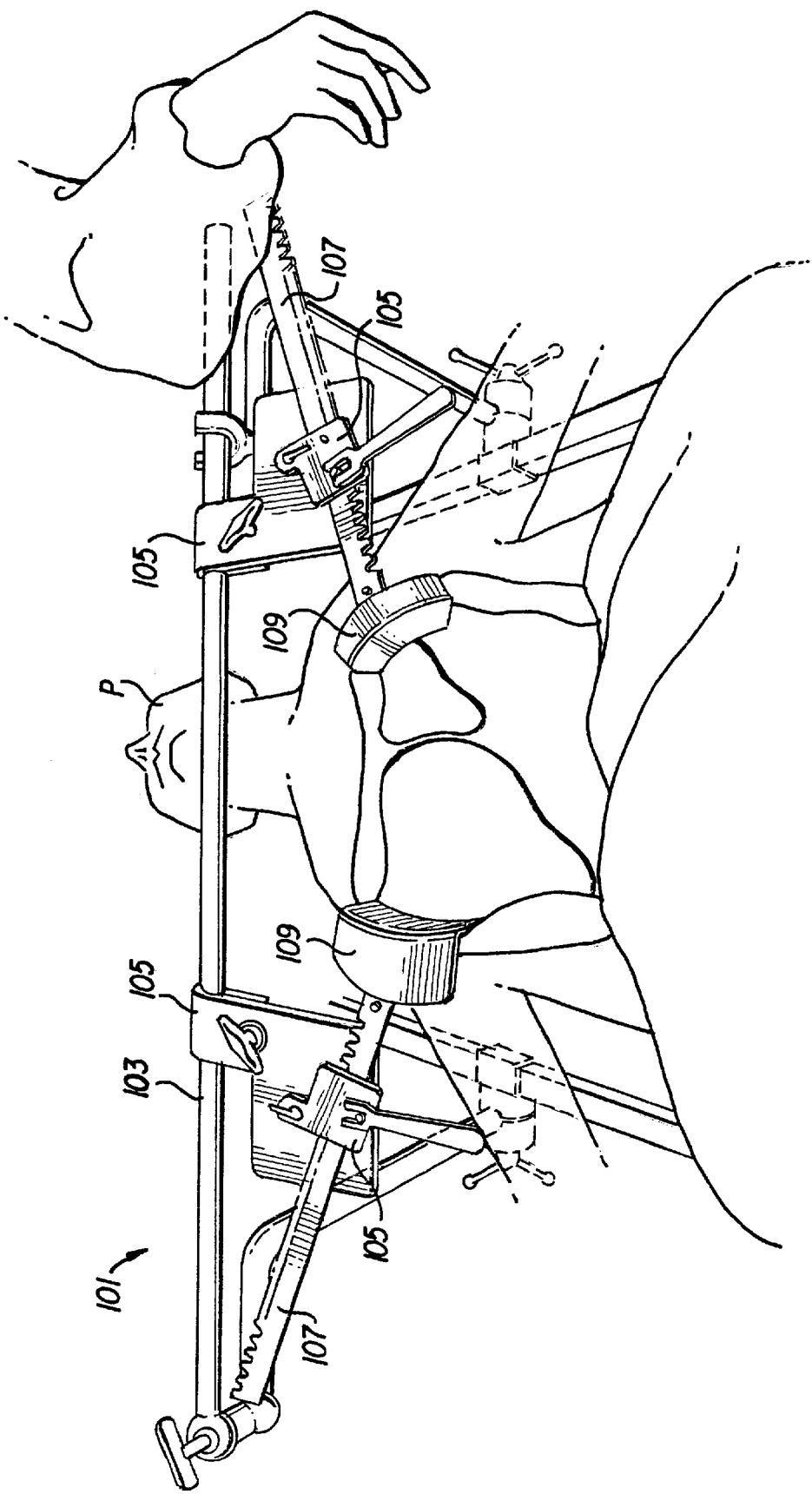
FIG. 1 shows a surgical assembly of the prior art in which retractor blades are used.
Figure 2:
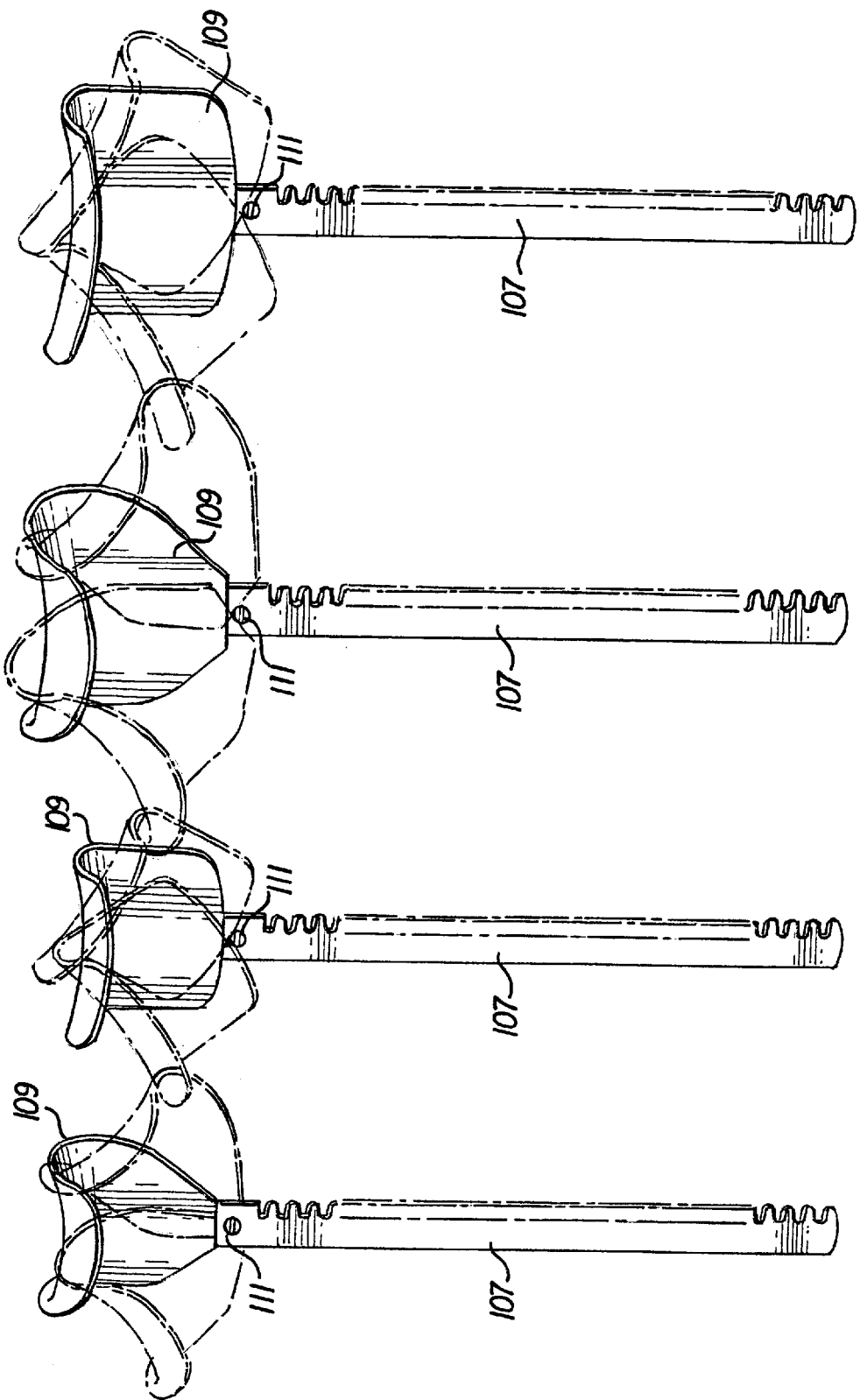
FIG. 2 shows various prior art retractor blades that are used in the assembly of FIG. 1 and their pivoting operations.
Figure 3:
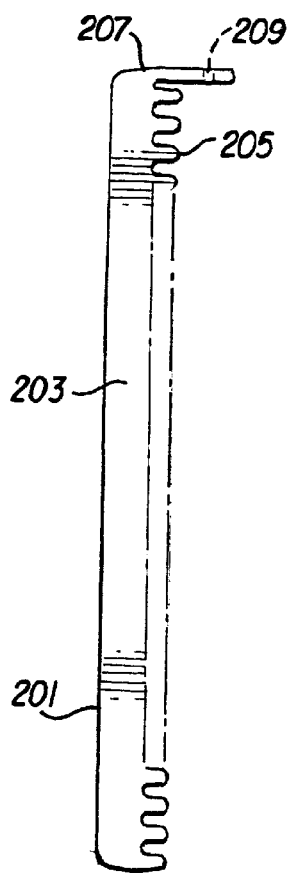
FIG. 3 shows a ratchet handle according to a first preferred embodiment of the present invention.

FIG. 3 shows a ratchet handle 201 according to the first preferred embodiment of the present invention. The ratchet handle 201 includes a ratchet portion 203 with ratchet teeth 205 and a bent portion 207 on one end. The bent portion can be bent in either direction with respect to the ratchet portion 203; in other words, a mirror image of the handle 201 can be made and used as needed. The bent portion 207 has a slot 209 for accommodating a blade in a manner to be explained below.

Figure 4:
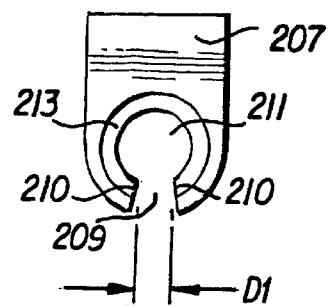
FIG. 4 shows a face-on view of a portion of the ratchet handle of FIG. 3.

FIG. 4 shows a face-on view of the bent portion 207. That view can be from either above or below the bent portion 207 in FIG. 3. The slot 209 is bounded by two sides 210 and leads to a circular opening 211 surrounded by a beveled portion 213. It is contemplated that both sides of the bent portion 207 will have beveled portions 213, although embodiments can be realized in which that is not the case. The slot 209 has a width D1.

Figure 5:
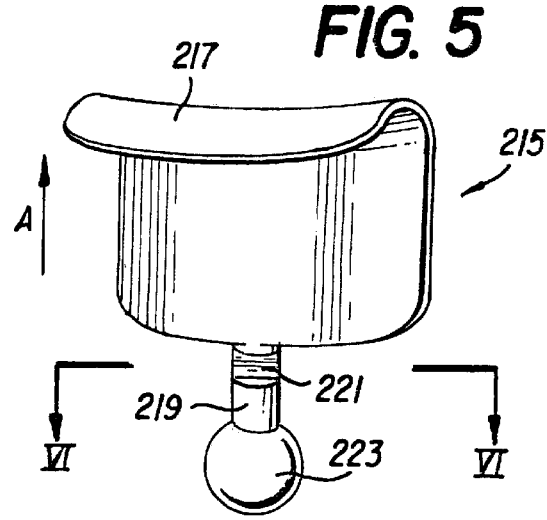
FIG. 5 shows a blade for use with the ratchet handle of FIG. 3.

FIG. 5 shows a blade 215 for use with the handle 201. The blade has a blade portion 217 that can have the same shape as any blade 109 of the prior art. The blade also has a cylindrical shaft 219 with flat portions 221 formed just below the point of attachment between the shaft 219 and the blade portion 217. The shaft 219 ends in a ball 223. Of course, multiple blades 215 can be provided in various shapes and sizes and used interchangeably.

Figure 6:
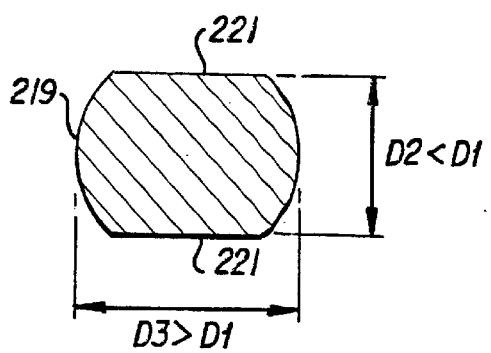
FIG. 6 shows a cross-sectional view of a shaft of the blade of FIG. 5.

FIG. 6 shows a cross-sectional view of the shaft 219 taken along lines VI—VI of FIG. 5. The cross-sectional view shows the flat portions 221 on both sides of the shaft 219. The flat portions 221 are separated by a distance D2 that is less than D1. Otherwise, the shaft 219 has a diameter D3 that is greater than D1.

The blade 215 is attached to the handle 201 in the following manner. The blade 215 is turned so that the flat portions 221 face the sides 210 of the slot 209. Since the slot 209 "sees" the shaft 219 as having a diameter D2, the shaft 219 easily slides through the slot 209 into the circular opening 211. Then the blade 215 is turned about 900. Since the slot 209 now "sees" the shaft 219 has having a diameter D3, the shaft 219 is retained in the circular opening 213. Furthermore, while the blade 215 is in use, the blade 215 is pulled relative to the ratchet handle 201 in the direction indicated by the arrow A in FIG. 5, so that the flat portions 221 are pulled away from the slot 209, thereby providing enhanced security against accidental detachment of the blade 215 from the handle 201. The ball 223 engages with the beveled portion 213 to form a ball-and-socket joint.

Figure 7:
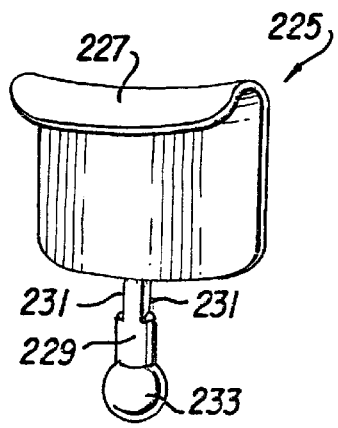
FIG. 7 shows an alternative construction of the blade of FIG. 5.

The flat portions do not have to be positioned as shown in FIG. 5. For example, another blade 225 shown in FIG. 7 has a blade portion 227, a shaft 229, flat portions 231, and a ball 233, like the corresponding components of the blade 215, except that the flat portions 231 are displaced by 900 relative to their position in the blade 215.

FIG. 8 shows a ratchet handle 301 according to the second preferred embodiment of the present invention. The ratchet handle 301 has a ratchet portion 303 with ratchet teeth 305 and a bent portion 307 on one end. The ratchet handle 301 is constructed like the ratchet handle 201 of FIG. 3, except that no slot 209 is provided. Thus, a blade attachment portion 315 is permanently retained.

FIG. 9 shows a cross-sectional view taken along the lines IX—IX of FIG. 8. Since there is no slot 209, the circular opening 311 is closed and is shown as being completely surrounded by the beveled portion 313. Thus, the shaft 317 of the blade attachment portion 315 is permanently retained in the circular opening 311.

Returning to FIG. 8, the blade attachment portion 315 will now be described. As already explained, the shaft 317 is retained in the circular opening 311. The shaft 317 ends in a ball 319. To allow assembly, the shaft 317 and the ball 319 can be provided on a separately formed lower portion 321 whose diameter, exclusive of the ball, is less than that of the circular opening 311. The lower portion 321 can be provided with flat portions 323, which function like the already disclosed flat portions 221 and 231, so that the blade attachment portion 315 can be provided separately for use with the blade handle 201 of the first preferred embodiment.

Attached to the lower portion 321 is an upper portion 325 for receiving a blade (not shown in FIG. 8). The upper portion 325 can receive and secure the blade with any suitable clamping mechanism, which can be tightened with a wing nut 327, an Allen wrench (not shown), or in any other suitable way.

A particular clamping mechanism will now be explained. FIG. 10 shows an exploded view of the blade attachment portion 315. The upper portion has a horizontal bore 329 and a vertical bore 331 that intersect to form a cruciform bore 333. A clamping portion 335 has a main body 337 with a vertical bore 339 therethrough and a screw portion 341. The clamping portion 335 is inserted into the horizontal bore 329, where a pin 343 in the upper portion 325 engages with a groove 345 in the clamping portion 335 to inhibit the clamping portion 335 in both rotation and lateral movement past a certain point. The screw portion 341 is then screwed into a threaded bore 347 in the finger-turning handle 327.

When the screw portion is still screwed fairly loosely into the threaded bore 347, the vertical bores 331 and 339 can be brought into alignment to allow insertion of a shaft of a blade or of any other tool that may be desired. When the wing nut 327 is tightened all the way, the clamping portion 335 is pulled as far to the right as the pin 343 and the groove 345 permit, thus moving the vertical bores 331 and 339 out of alignment to clamp down on such a shaft. That operation will be familiar to those skilled in the art from the above-cited patent to Meier et al.

FIG. 11 shows a blade 349 suitable for use with the ratchet handle 301 and the attachment portion 315. The blade 349 has a blade portion 351 that can be the same as those of the prior art. Extending from the blade portion 351 is a smooth shaft 353 adapted for use with the clamping mechanism of the attachment portion 315. The shaft 353 has a diameter selected such that when the vertical bores 331 and 339 are aligned, the shaft is easily inserted into the vertical bores 331 and 339, but such that when the wing nut 327 is tightened all the way, the clamping portion 335 securely holds the shaft 353. It will be readily appreciated that any other type of shaft can be provided for use with whatever clamping mechanism is used in the attachment portion 315.

While two preferred embodiments have been set forth above, those skilled in the art who have reviewed the present disclosure will readily appreciate that other embodiments can be realized within the scope of the invention. For example, any other joint allowing more than one degree of freedom can be used, and the blade and ratchet handle can be attached in any other permanent or separable way. Therefore, the present invention should be construed as limited only by the appended claims.

What is claimed is:

1. A surgical retractor blade and handle assembly comprising:

a surgical retractor blade;

a handle; and attaching means for removably attaching the surgical retractor blade to the handle such that the surgical retractor blade moves relative to the handle with more than one degree of freedom by forming a ball and socket joint between the surgical retractor blade and the handle such that the surgical retractor blade moves relative to the handle with at least two degrees of freedom; wherein said attaching means comprises:

on the surgical retractor blade, a shaft ending in a ball; and on the handle, a portion with (i) a circular opening for engaging with the ball to define the ball and socket joint and (ii) a slot extending from the circular opening for receiving the shaft for engaging the ball with the opening and disengaging the ball from the opening; and wherein:

the slot has a width D1;

the shaft has a diameter D2 in a first direction and a diameter D3 in a second direction; and

D2<D1<D3.

2. The assembly of claim 1, wherein the handle is a ratchet handle.

3. A surgical retractor blade and handle assembly comprising:

a surgical retractor blade;

a handle; and attaching means for removably attaching the surgical retractor blade to the handle such that the surgical retractor blade moves relative to the handle with more than one degree of freedom;

the attaching means comprising:

ball and socket means for forming a permanent ball and socket joint between the surgical retractor blade and the handle such that the surgical retractor blade moves relative to the handle with at least two degrees of freedom, such that the attaching means is permanently attached to the surgical retractor blade through the ball and socket means; and means for removably attaching the surgical blade to the ball and socket means.

* * * * *